United States Patent [19]

Downey

[11] Patent Number: 4,926,849

[45] Date of Patent: May 22, 1990

[54] APPARATUS FOR SEPARATING VERTEBRAE

[76] Inventor: Ernest L. Downey, 10559 S. Ave. G, Chicago, Ill. 60617

[21] Appl. No.: 943,481

[22] Filed: Dec. 19, 1986

[51] Int. Cl.[5] ............................................. A61B 17/00
[52] U.S. Cl. ........................................ 128/75; 128/20; 128/69; 606/86
[58] Field of Search ............ 128/20, 3, 69, 75, 92 ZZ, 128/92 ZY, 92 ZK, 303 R, 92 V

[56] References Cited

U.S. PATENT DOCUMENTS

| | | | |
|---|---|---|---|
| 2,642,862 | 6/1953 | Jackson | 128/20 |
| 3,572,326 | 3/1971 | Jensen | 128/20 |
| 4,505,268 | 3/1985 | Sgandurra | 128/69 |
| 4,611,582 | 9/1986 | Duff | 128/69 |
| 4,627,421 | 12/1986 | Symbas et al. | 128/20 |

Primary Examiner—Michael H. Thaler

[57] ABSTRACT

An apparatus useful to separate adjacent first and second vertebrae during surgery comprising: a support, first and second grips associated with the support and being sized and structured to grip the first and second vertebrae, respectively; and a first movement assembly associated with the first grip and being capable of being operated to move the first grip to a desired position and to hold the first grip in the desired location.

16 Claims, 1 Drawing Sheet

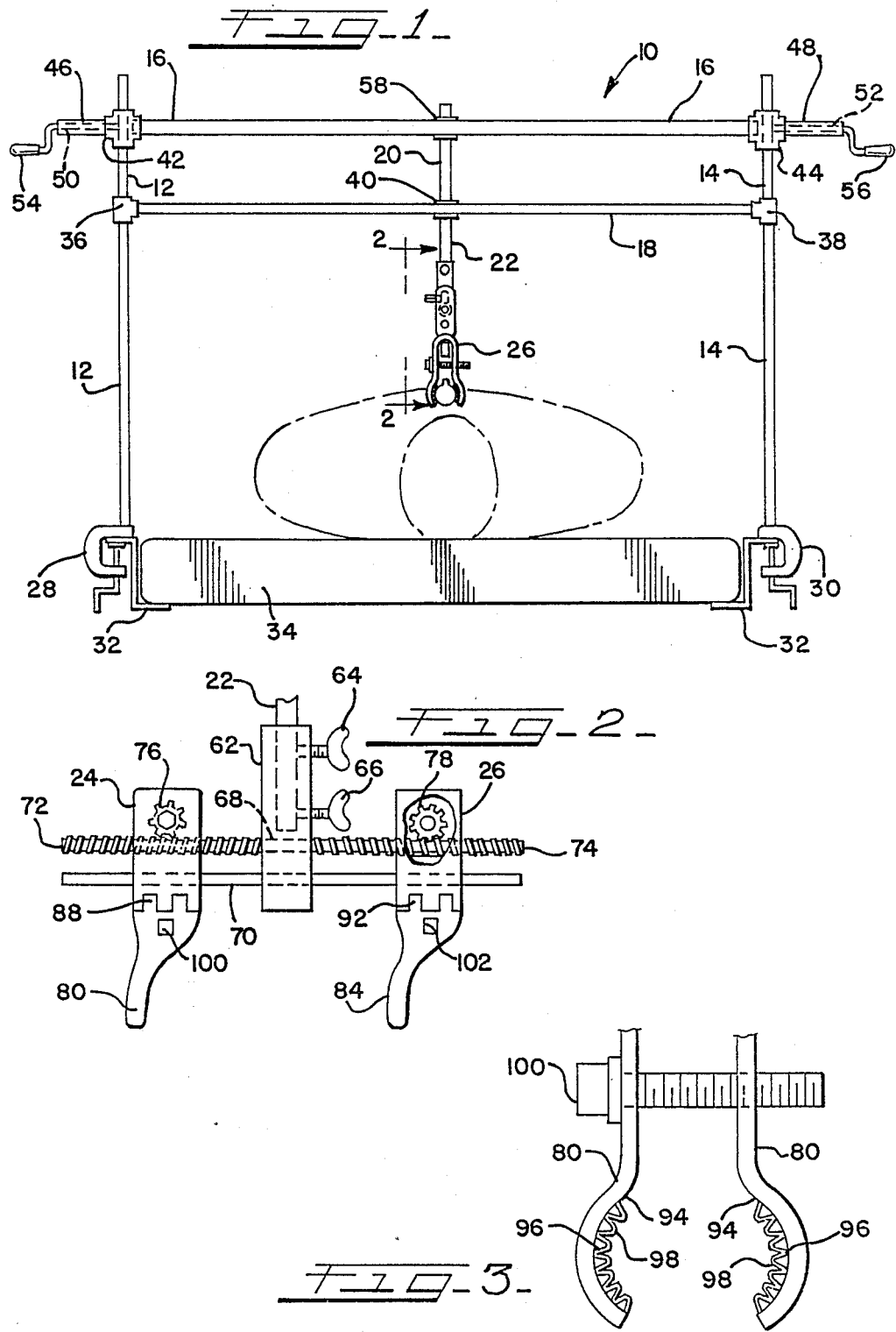

APPARATUS FOR SEPARATING VERTEBRAE

The present invention relates to an apparatus useful for separating vertebrae. More particularly, this invention relates to an apparatus useful for separating adjacent vertebrae during surgery, e.g., for repair or removal of disk material.

One of humankind's major medical problems involves various difficulties with the back. In particular, back concerns may involve the vertebrae which are cushioned by discs which are positioned between the individual vertebra. Because of exertion, illness, accident or abuse, one or more of these discs (or at least a portion of the disc material making up the discs) becomes ruptured or otherwise requires repair or, more often, removal. For example, if a disc is ruptured, at least a portion of the disc material is forced into contact with the spinal cord and/or other sensitive nerves. This contact causes excruciating pain which makes it advantageous to alleviate this condition.

The ruptured disc may be surgically removed and the two vertebrae from between which the disc was removed being fused. Since the back, and in particular the spinal area, is delicate and sensitive, it would be advantageous to provide an apparatus to make such disc repair/removal surgery effective.

Therefore, one object of the present invention is to provide an apparatus useful to separate adjacent vertebrae during surgery.

Another object of the present invention is to provide a method for separating adjacent vertebrae during surgery. Other objects and advantages of the present invention will become apparent hereinafter.

An improved apparatus and method useful to separate adjacent first and second vertebrae during surgery, e.g., disc repair/removal surgery, has been discussed. In one broad embodiment, the present apparatus comprises: support means; first and second grip means associated, preferably adjustably secured to, the support means and structured to grip the first vertebra and the second vertebra, respectively; and movement means associated with the first grip means and being capable of being operated, preferably manually operated, to move the first grip means to a desired position and to hold the first grip means in the desired position.

The present invention provides substantial advantages. For example, the present vertebrae separating apparatus is relatively easy to use, gives the surgeon effective and precise control over the degree of vertebrae separation to be used in any particular surgery, and allows the surgeon to concentrate his/her efforts in safely repairing/removing the disc material between the two separated vertebrae. In short, the device of this invention provides for easily and precisely controlled separating of vertebrae during surgery with the overall effect of aiding the surgeon's performance.

Preferably, the present system further comprises second movement means associated with the second grip means and being capable of being operated, preferably manually operated, to move the second grip means to a desired position and to hold the second grip means in this desired position. Having a first and second movement means provides improved flexibility and gives the surgeon the ability to move both vertebrae to be separated to new positions, as desired. Still further increased flexibility is achieved in the event, as is more preferred, that the first and second movement means are capable of being operated, e.g., moved to desired positions, independently of each other.

In one embodiment, the first movement means, or each of the first and second movement means, comprises a gear assembly with teeth and a threaded rod. The gear assembly and threaded rod are structured so that the teeth of the gear assembly mesh with the threads of the rod. Turning the gear assembly causes the first or second grip means to move along the threaded rod. A conventional ratchet wrench, or comparable device, may be used to precisely control the turning of the gear assembly and, ultimately, the position of the first or second grip means and first or second vertebra. The gear assembly and threaded rod are preferably structured so that the natural tendency of the vertebrae being held by the grip means to resist separation is insufficient to move the grip means from the desired position. In one particular embodiment, the present gear assembly includes a lock which can be manually activated to lock the grip means at the desired position, e.g., at a desired position on the threaded rod.

Preferably, the same threaded rod is used in both the first and second movement means. This provides for ease of fabrication and, more importantly, ease of alignment between the first and second grip means. This alignment is important so that stress on the spinal column in general is minimized. In one particular embodiment, the threads of the rod on which the first grip means moves are oriented substantially opposite from the threads on which the second grip means moves. For example, one set of threads can be right hand threads while the other threads are left hand threads. This embodiment is especially easy to operate since turning each of the gear assemblies in one direction results in increased vertebrae separation, while turning the gear assemblies in the opposite direction results in decreased vertebrae separation.

An additional stabilizing means is preferably included. This stabilizing means, more preferably a straight, unthreaded rod, is associated with the support means and the first and second grip means, and acts to at least aid in maintaining the desired alignment between the first and second grip means. The importance of maintaining this alignment is discussed elsewhere herein.

The first and second grip means are each preferably capable of being opened to receive or release the first and second vertebrae, respectively, and capable of being closed to grip the first and second vertebrae, respectively. This feature reduces the changes of permanently damaging the first and second vertebrae as a result of using the present apparatus. In one particular embodiment, each of the first and second grip means includes a bolt-hinge assembly to facilitate this opening and closing.

Each of the first and second grip means preferably includes a plurality of gripping teeth acting to facilitate the gripping and holding of the first and second vertebrae by the first and second grip means, respectively. These gripping teeth are preferably structured to be effective but, also, to reduce the risk of permanent damage to the first and second vertebrae as a result of using the present apparatus. In one particular embodiment, the gripping teeth are padded, e.g., with a relatively soft material which acts as a cushion between the first or second vertebra and the gripping teeth of the first or second grip means, respectively.

The first and second grip means are preferably curved to reduce the risk of permanent damage to the vertebrae from using the present apparatus. The human vertebra includes an accessor process, a transverse process and an oddly shaped knuckle which extends generally outwardly from the human's back. These processes (or wings) and knuckle are particularly prone to damage and, thus, it is preferred not to grip these portions of the vertebra with the present grip means. The preferred curvature of the first and second grip means allows the vertebrae to be effectively gripped and held, while avoiding the wings and knuckle of the vertebrae. If gripping teeth are employed, it is preferred that such gripping teeth be located on concave surfaces of the first and second grip means. The gripping means, in particular the gripping teeth, preferably grip the body of the vertebrae.

The support means, as its name implies, is structured to support the first and second grip means. The support means is preferably adjustable to control the height and position of the first and second grip means. For example, the support means may be structured to be clamped to the table on which the surgery is being performed, i.e., the operating table. In one particular embodiment, the support means includes a first and a second height control means. The first height control means acts to control the gross height of the first and second grip means. The second height control means acts to control the fine height of the first and second grip means, e.g., acts as a "fine tune" on the height of the first and second grip means. The support means is preferably structured to reduce torque forces acting on the first and second grip means. This, in turn, reduces the stress on the first and second vertebrae being held by the first and second grip means, respectively. For example, the portion of the support means directly associated to the first and second grip means is preferably structured, e.g., of materials having rectangular cross-sections, to reduce the risk of the first and second grip means turning while in use.

These and other aspects and advantages of the present invention are set forth in the following detailed description and claims, particularly when considered in conjunction with the accompanying drawings in which like parts bear like reference numerals. In the drawings:

FIG. 1 is a front view showing one embodiment of the present apparatus in use.

FIG. 2 is elevation view taken along line 2—2 of FIG. 1.

FIG. 3 is a front elevation view showing, in more detail, certain components of the embodiment shown in FIG. 1.

Referring to the drawings, a vertebrae separator, shown generally at 10, includes left upright bar 12, right upright bar 14, top cross bar 16, bottom cross bar 18, middle bar 20, center piece 22, and first and second grippers 24 and 26, respectively. Left and right upright bars 12 and 14 are fixedly secured to left and right clamps 28 and 30, respectively, which are in turn clamped onto the frame 32 of operating table 34.

Left and right upright bars 12 and 14 are coplanar and mutually parallel and are perpendicular to the plane of operating table 34. Left and right T-fittings 36 and 38 are slideably associated with left and right upright bars 12 and 14, respectively. That is, left and right T-fittings 36 and 83 can slide freely up and down left and right upright bars 12 and 14. Bottom cross bar 18 is fixedly secured to both left and right T-fittings 36 and 38 and also to bottom fitting 40.

Top cross bar 16 is fixedly secured to left and right cross-fittings 42 and 44. Also associated with left and right cross fittings 42 and 44 are left and right threaded pipes 46 and 48. Left and right threaded stoppers 50 and 52 are matingly engaged with the threads of left and right threaded pipes 46 and 48, respectively. Left and right turn cranks 54 and 56 are secured to left and right threaded stopers 50 and 52, respectively, and can be manually turned to bring left and right threaded stoppers 50 and 52 in and out of contact with left and right upright bars 12 and 14, respectively. When left and right threaded stoppers 50 and 52 are not in contact with left and right upright bars 12 and 14, respectively, left and right upright bars 12 and 14 can slide freely in left and right cross-fittings 42 and 44, respectively. However, when left and right threaded stoppers 50 and 52 are brought into contact with left and right upright bars 12 and 14, respectively, left and right cross fittings 42 and 44 are held stationary relative to left and right upright bars 12 and 14, respectively. By controlling this contacting and choosing at what points on left and right upright bars 12 and 14 left and right cross-fittings 42 and 44, respectively, are to be held, the gross height of first and second grippers 24 and 26 relative to operating table 34 can be controlled.

Top cross bar 16 and bottom cross bar 18 are each perpendicular to left and right upright bars 12 and 14. Top cross bar 16 is fixedly secured to both left and right cross fittings 42 and 44 and also to top fitting 58. The distance between top cross bar 16 and bottom cross bar 18 is fixed. Middle bar 20 is parallel to and coplanar with both left and right upright bars 12 and 14 and is fixedly secured to both top fitting 58 and bottom fitting 40.

Center piece 22 is fixedly secured to and extends downwardly from bottom fitting 40. Center piece 22, which has a square cross-section to avoid twisting, is parallel to and coplanar with left and right upright bars 12 and 14. Center piece 22 is fitted into a receiving member 62 which is associated with two threaded wing nuts 64 and 66. Center piece 22 can be inserted into receiving member 62 and threaded wing nuts 64 and 66 can be brought into contact with center piece 22 to hold center piece 22 in place in receiving member 64. The length of center piece 22 inserted and held in receiving member 64 can be varied, as desired. By controlling this degree of insertion, the height of first and second grippers 24 and 26 can be finely controlled.

Receiving member has a threaded rod 68 and a stabilizing rod 70 fixedly secured to it and extending in a direction perpendicular to center piece 22. Stabilizing rod 70 extends through both first gripper 24 and second gripper 26 which are slideable on stabilizing rod 70. This stabilizing rod 70 acts in maintaining the alignment of first and second grippers 24 and 26. Threaded rod 68 includes a first portion 72, which extends through first gripper 24, and a second portion 74, which extends through second gripper 26. First gripper 24 includes a first worm gear 76 the teeth of which mesh with the threads of first portion 72. Similarly, second gripper 26 includes a second worm gear 78 the teeth of which mesh with the threads of second portion 74. First and second worm gears 76 and 78 can each be turned by conventional ratchets to cause independent movement of first and second worm gears along threaded rod 68. In this manner, first and second grippers 24 and 26 are moved independently along threaded rod 68, as desired. The threads on first portion 72 and on second portion 74 are positioned in substantially opposite directions. This allows one to move first and second grippers 24 and 26 in the same direction by turning first and second worm gears 76 and 78, respectively, in the same direction. The threads of first and second portions 72 and 74 and the teeth of first and second worm gears 76 and 78 are structured to remain engaged (or locked) in position until turned by a ratchet.

First gripper 24 includes two downwardly depending, curved and hinged first legs 80. Second gripper 26 includes two downwardly depending, curved and hinged second legs 84. First hinges 88 act to allow first hinged legs 80 to open and close, as desired. Similarly, second hinges 92 act to allow second hinged legs 84 to open and close, as desired. Each of first second legs 80 and 84 are curve d*to provide an interior concave surface 94 on which is located a plurality of gripping teeth 96. A protective padding 88 is adhesively secured to each of the groups of gripping teeth 96. First and second threaded bolts 100 and 102 are placed into threaded holes of first and second legs 80 and 84, respectively. If it is desired to close and lock first and second legs 80 and 84 around a vertebra, first and second legs 80 and 84 are placed around the vertebra involved and each bolt 100 and 102 is threaded into the threaded holds of first and second legs 80 and 84 until first and second legs securely grip and hold the vertebra.

Vertebrae separator 10 functions as follows. The patient who is to be operated on is placed on his/her stomach on operating table 34. Separator 10 is moved and clamped into place. The surgeon, after making the required incision, secures first gripper 24 to one vertebra and second gripper 26 to an adjacent vertebra. The curvature of first and second legs 80 and 84 allows the vertebrae bodies to be gripped without contacting the especially delicate or fragile wings or knuckles of the vertebrae. Then, using a conventional ratchet, the surgeon causes first and second grippers 24 and 26 to move in opposite directions along threaded rod 68 to separate the two vertebrae. After the desired degree of separation is achieved, the surgeon is able to correct the diagnosed problem, e.g., removal of disc material between the two vertebrae, while the two vertebrae are separated. Once this is accomplished, the first and second grippers 24 and 26 are ratcheted back to the original positions and the two vertebrae are released from first and second grippers 24 and 26 (by loosening first and second bolts 100 and 102, respectively).

While this invention has been described with respect to various specific examples and embodiments, it is to be understood that the invention is not limited thereto and that it can be practiced within the scope of the following claims.

The embodiments of the present invention in which an exclusive property or privilege is claimed are as follows:

1. An apparatus useful to separate adjacent first and second vertebrae during surgery comprising:
   support means; first and second grip means associated with said support means and being sized and structured to grip said first vertebra and said second vertebra, respectively;
   first movement means associated with said first grip means and structured to be manually operated while said first grip means is gripping said first vertebra and said second grip means is gripping said second vertebra to move said first grip means to a desired position relative to said second grip means, to separate said first and second vertebrae and to hold said first grip mean in said desired position; and
   second movement means associated with said second grip means and structured to be manually operated independent of said first movement means while said first grip means is gripping said first vertebra and said second grip means is gripping said second vertebra to move said second grip means to a desired position relative to said first grip means, to separate said first and second vertebrae and to hold said second grip means in said desired position.

2. The apparatus of claim 1 wherein said first movement means comprises a gear assembly and a threaded rod adapted so that the teeth of said gear assembly mesh with the threads of said threaded rod, and turning said gear assembly causes said first grip means to move along said threaded rod.

3. The apparatus of claim 1 wherein each of said first and second movement means comprise a gear assembly and a threaded rod adapted so that the teeth of said gear assembly mesh with the threads of said threaded rod, and turning said gear assembly causes said first or second grip means to move along said threaded rod.

4. The apparatus of claim 3 wherein the same threaded rod is used in both said first and second movement means.

5. The apparatus of claim 1 which further comprises a stabilizing means associated with said support means and said first and second grip means, and acting to at least aid in maintaining the desired alignment between said first and second grip means.

6. The apparatus of claim 1 wherein each of said first and second grip means includes two legs capable of being opened to receive or release said first and second vertebrae, respectively, and capable of being closed to grip said first and second vertebrae, respectively.

7. The apparatus of claim 6, wherein each of said first and second grip means includes a bolt-hinge assembly to facilitate said opening and closing of said legs.

8. The apparatus of claim 6 wherein each of said first and second legs are curved to allow said first and second vertebrae, respectively, to be gripped without contacting the wings or knuckles of said first and second vertebrae.

9. The apparatus of claim 1 wherein each of said first and second grip means includes a plurality of gripping teeth acting to facilitate the gripping and holding of said first and second vertebrae by said first and second grip means, respectively.

10. The apparatus of claim 9 wherein said gripping teeth are structured to reduce the risk of permanent damage to said first and second vertebrae.

11. The apparatus of claim 10 wherein said gripping teeth are padded.

12. The apparatus of claim 10 wherein said gripping teeth are located on concave surfaces.

13. The apparatus of claim 1 wherein said first and second grip means are curved to reduce the risk of permanent damage to said first and second vertebrae.

14. The apparatus of claim 1 wherein said support means is adjustable to control the height and position of said first and second grip means.

15. The apparatus of claim 1 wherein said support means includes a first and a second height control means, said first height control means acting to control the gross height of said first and second grip means, and said second height control means acting to control the fine height of said first and second grip means.

16. The apparatus of claim 1 wherein said support means is structured to be clamped to the table on which said surgery is being performed.

* * * * *

UNITED STATES PATENT AND TRADEMARK OFFICE
CERTIFICATE OF CORRECTION

PATENT NO. : 4,926,849
DATED : May 22, 1990
INVENTOR(S) : Downey

It is certified that error appears in the above—identified patent and that said Letters Patent is hereby corrected as shown below:

Column 1, line 8; delete "disk" and insert in place thereof --disc--

Column 2, line 51; delete "changes" and insert in place thereof --chances--

Column 4, line 10; delete "stopers" and insert in place thereof --stoppers--

Column 4, line 46 and line 48; delete "64" and insert in place thereof --62--

Column 5, line 17; delete "curve d*" and insert in place thereof --curved--

Signed and Sealed this

Twenty-third Day of July, 1991

Attest:

HARRY F. MANBECK, JR.

*Attesting Officer*     *Commissioner of Patents and Trademarks*